United States Patent [19]

Barker

[11] Patent Number: 5,475,001
[45] Date of Patent: Dec. 12, 1995

[54] QUINAZOLINE DERIVATIVES

[75] Inventor: Andrew J. Barker, Macclesfield, United Kingdom

[73] Assignee: Zeneca Limited, London, England

[21] Appl. No.: 272,390

[22] Filed: Jul. 19, 1994

[30] Foreign Application Priority Data

Jul. 19, 1993 [GB] United Kingdom ............... 9314893

[51] Int. Cl.$^6$ .................. C07D 239/86; A61K 31/505
[52] U.S. Cl. ............................ 514/258; 544/293
[58] Field of Search ................ 544/293; 514/259

[56] References Cited

U.S. PATENT DOCUMENTS

| | | | |
|---|---|---|---|
| 4,322,420 | 3/1982 | Kobayashi et al. | 514/259 |
| 4,464,375 | 8/1984 | Kobayashi et al. | 514/259 |

FOREIGN PATENT DOCUMENTS

| | | |
|---|---|---|
| 0516588 | 12/1992 | European Pat. Off. . |
| 0520722 | 12/1992 | European Pat. Off. . |
| 0566226 | 10/1993 | European Pat. Off. . |
| 520722 | 10/1993 | European Pat. Off. . |
| 0602851 | 6/1994 | European Pat. Off. . |
| 56-20577 | 2/1981 | Japan . |
| 59-13765 | 1/1984 | Japan . |
| 2033894 | 5/1980 | United Kingdom . |
| 9214716 | 9/1992 | WIPO . |
| 9220642 | 11/1992 | WIPO . |

OTHER PUBLICATIONS

Chemical Abstracts, vol. 95, No. 1, 6, Jul. 1981, p. 682, 7199a.
Iyer et al., Studies in Potential Amoebicides: . . . 8-Hydroxy(&8-Methoxy)-4-Quinazolones, J. Sci. Industri. Res., Jan. 1956, pp. 1-7.
Chemical Abstract 98, 89384x and Derwent Abstract 87077 E/41 of Japan 57-144266, Sep. 1982.
Chemical Abstract 92, 76445u, Li et al., Synthesis of shangrolin analogs as antimalarials, 1979.
Chemical Abstract 96, 122728w, Lin et al., Studies on antiarrythmics . . . , 1981.

*Primary Examiner*—Mukund J. Shah
*Assistant Examiner*—Matthew V. Grumbling
*Attorney, Agent, or Firm*—Cushman Darby & Cushman

[57] ABSTRACT

The invention concerns quinazoline derivatives of the formula I

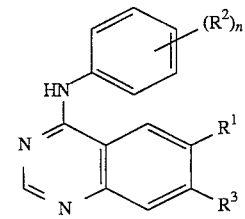

wherein $R^1$ includes hydroxy, amino, hydroxyamino, (1–4C)alkoxy, (1–4C)alkylamino and di-[(1–4C)alkyl]amino;
$R^3$ is halogeno;
n is 1, 2 or 3 and $R^2$ includes hydrogen, hydroxy, halogeno and (1–4C)alkyl;
or a pharmaceutically-acceptable salt thereof;

processes for their preparation; pharmaceutical compositions containing them; and the use of the receptor tyrosine kinase inhibitory properties of the compounds in the treatment of cancer.

15 Claims, No Drawings

QUINAZOLINE DERIVATIVES

The invention relates to quinazoline derivatives, or pharmaceutically-acceptable salts thereof, which possess anticancer activity and are accordingly useful in methods of treatment of cancer in the human or animal body. The invention also relates to processes for the manufacture of said quinazoline derivatives, to pharmaceutical compositions containing them and to their use in the manufacture of medicaments of use in the production of an anti-cancer effect in a warm-blooded animal such as man.

Many of the current treatment regimes for cancer utilise compounds which inhibit DNA synthesis. Such compounds are toxic to cells generally but their toxic effect on the rapidly dividing tumour cells can be beneficial. Alternative approaches to anti-cancer agents which act by mechanisms other than the inhibition of DNA synthesis have the potential to display enhanced selectivity of action against cancer cells.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor and an intracellular portion which functions as a kinase to phosphorylate tyrosine amino acids in proteins and hence to influence cell proliferation. It is known that such kinases are frequently present in common human cancers such as breast cancer (Sainsbury et al., *Brit. J. Cancer*, 1988, 58, 458; Guerin et al., *Oncogene Res.*, 1988, 3, 21), gastrointestinal cancer such as colon, rectal or stomach cancer (Bolen et al., *Oncogene Res.*, 1987, 1, 149), leukaemia (Konaka et al., *Cell*, 1984, 37, 1035) and ovarian, bronchial or pancreatic cancer (European Patent Specification No. 0400586). As further human tumour tissues are tested for receptor tyrosine kinase activity it is expected that its widespread prevalance will be established in further cancers such as thyroid and uterine cancer. It is also known that tyrosine kinase activity is rarely detected in normal cells whereas it is more frequently detectable in malignant cells (Hunter, *Cell*, 1987, 50, 823). It has been shown more recently (W J Gullick, *Brit. Med. Bull.*, 1991, 47, 87) that epidermal growth factor receptor which possesses tyrosine kinase activity is overexpressed in many human cancers such as brain, lung squamous cell, bladder, gastric, breast, head and neck, oesophageal, gynaecological and thyroid tumours.

Accordingly it has been recognised that an inhibitor of receptor tyrosine kinase should be of value as a selective inhibitor of the growth of mammalian cancer cells (Yaish et al. *Science*, 1988, 242, 933). Support for this view is provided by the demonstration that erbstatin, a receptor tyrosine kinase inhibitor, specifically attenuates the growth in athymic nude mice of a transplanted human mammary carcinoma which expresses epidermal growth factor (EGF) receptor tyrosine kinase but is without effect on the growth of another carcinoma which does not express EGF receptor tyrosine kinase (Toi et al., *Eur. J. Cancer Clin. Oncol.*, 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives has been demonstrated against the growth of human squamous cell carcinoma inoculated into nude mice (Yoneda et al., *Cancer Research*, 1991, 51, 4430). Accordingly it has been indicated that receptor tyrosine kinase inhibitors will prove to be useful in the treatment of a variety of human cancers. Various known tyrosine kinase inhibitors are disclosed in a more recent review by T R Burke Jr. (*Drugs of the Future*, 1992, 17, 119).

We have now found that certain quinazoline derivatives possess anti-cancer properties which are believed to arise from their receptor tyrosine kinase inhibitory properties.

It is known from the patent application WO 92/20642 that certain aryl and heteroaryl compounds inhibit receptor tyrosine kinase. There is the disclosure of certain quinazoline derivatives but no mention is made of 4-anilinoquinazoline derivatives.

It is also known from European Patent Application No. 92305703.8 (publication no. 0 520 722) that certain 4-anilinoquinazoline derivatives which are unsubstituted at positions 5 to 8 of the quinazoline ring or which bear a halogeno, trifluoromethyl or nitro substituent at one of those positions are useful as inhibitors of receptor tyrosine kinase. There is no disclosure in that Application of 4-anilinoquinazoline derivatives which bear an amino, alkylamino, acylamino or alkoxy substituent at any of positions 5 to 8.

We have now discovered that certain 4-anilinoquinazoline derivatives which bear a halogeno substituent at the 7-position and which also bear an amino, alkylamino, acylamino or alkoxy substituent at the 6-position are useful as inhibitors of receptor tyrosine kinase.

According to the invention there is provided a quinazoline derivative of the formula I (set out hereinafter) wherein $R^1$ is hydroxy, amino, hydroxyamino, trifluoromethoxy, (1–4C)alkoxy, (1–4C)alkylamino, di-[(1–4C)alkyl]amino, aziridin-1-yl, azetidin-1-yl, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, phenyl-(1–4C)alkoxy, halogeno-(2–4C)alkylamino, hydroxy-(2–4C)alkylamino, (1–4C)alkoxy-(2–4C)alkylamino, phenyl-(1–4C)alkylamino, (2–4C)alkanoylamino, benzamido, 2-oxopyrrolidin-1-yl, 2-oxopiperidin-1-yl, halogeno-(2–4C)alkanoylamino, hydroxy-(2–4C)alkanoylamino, (1–4C)alkoxy-(2–4C)alkanoylamino, (3–4C)alkenoylamino, (3–4C)alkynoylamino, N-(1–4C)alkyl-(2–4C)alkanoylamino, N-(1–4C)alkylbenzamido, N-(1–4C)alkyl-halogeno-(2–4C)alkanoylamino, N-(1–4C)alkyl-hydroxy-(2–4C)alkanoylamino, N-(1–4C)alkyl-(1–4C)alkoxy-(2–4C)alkanoylamino, N-(1–4C)alkyl-(3–4C)alkenoylamino or N-(1–4C)alkyl-(3–4C)alkynoylamino, and wherein said benzamido or N-(1–4C)alkylbenzamido substituent or any phenyl group in a $R^1$ substituent may optionally bear one or two halogeno, (1–4C)alkyl or (1–4C)alkoxy substituents; $R^3$ is halogeno; and n is the integer 1, 2 or 3 and each $R^2$ is independently hydrogen, hydroxy, halogeno, trifluoromethyl, amino, nitro, cyano, (1–4C)alkyl, (1–4C)alkoxy or (2–4C)alkanoylamino; or a pharmaceutically-acceptable salt thereof.

The chemical formulae referred to herein by Roman numerals are set out for convenience on a separate sheet hereinafter. In this specification the term "alkyl" includes both straight and branched chain alkyl groups but references to individual alkyl groups such as "propyl" are specific for the straight chain version only. An analogous convention applies to other generic terms.

Within the present invention it is to be understood that a quinazoline of the formula I may exhibit the phenomenon of tautomerism and that the formulae drawings within this specification can represent only one of the possible tautomeric forms. It is to be understood that the invention encompasses any tautomeric form which possesses anti-cancer activity and is not to be limited merely to any one tautomeric form utilised within the formulae drawings.

The quinazolines of the formula I are unsubstituted at the 2-, 5- and 8-positions.

It is also to be understood that certain quinazolines of the formula I can exist in solvated as well as unsolvated forms such as, for example, hydrated forms. It is to be understood that the invention encompasses all such solvated forms which possess anti-cancer activity.

According to a further aspect of the invention there is provided a quinazoline derivative of the formula I wherein $R^1$ is hydroxy, amino, hydroxyamino, trifluoromethoxy, (1–4C)alkoxy, (1–4C)alkylamino, di-[(1–4C)alkyl]amino, aziridin-1-yl, azetidin-1-yl, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, phenyl-(1–4C)alkoxy, halogeno-(2–4C)alkylamino, hydroxy-(2–4C)alkylamino, (1–4C)alkoxy-(2–4C)alkylamino, phenyl-(1–4C)alkylamino, (2–4C)alkanoylamino, benzamido, 2-oxopyrrolidin-1-yl, 2-oxopiperidin-1-yl, halogeno-(2–4C)alkanoylamino, hydroxy-(2–4C)alkanoylamino or (1–4C)alkoxy-(2–4C)alkanoylamino, and wherein said benzamido substituent or any phenyl group in a $R^1$ substituent may optionally bear one or two halogeno, (1–4C)alkyl or (1–4C)alkoxy substituents; $R^3$ is halogeno; and n is the integer 1, 2 or 3 and each $R^2$ is independently hydrogen, hydroxy, halogeno, trifluoromethyl, amino, nitro, cyano, (1–4C)alkyl, (1–4C)alkoxy or (2–4C)alkanoylamino; or a pharmaceutically-acceptable salt thereof.

Suitable values for the generic radicals referred to above include those set out below.

A suitable value for $R^2$ when it is (1–4C)alkyl is, for example, methyl, ethyl, propyl, isopropyl, butyl, isobutyl, sec-butyl or tert-butyl; when it is (1–4C)alkoxy is, for example, methoxy, ethoxy, propoxy, isopropoxy or butoxy; and when it is (2–4C)alkanoylamino is, for example, acetamido, propionamido or butyramido.

Suitable values for each $R^1$ substituent which may be present on the quinazoline ring include, for example:
for (1–4C)alkoxy: methoxy, ethoxy, propoxy, isopropoxy and butoxy;
for (1–4C)alkylamino: methylamino, ethylamino and propylamino;
for di-[(1–4C)alkyl]amino: dimethylamino, diethylamino, N-ethyl-N-methylamino and dipropylamino;
for (1–4C)alkylthio: methylthio, ethylthio and propylthio;
for 4-(1–4C)alkylpiperazin-1-yl: 4-methylpiperazin-1-yl and 4-ethylpiperazin-1-yl;
for halogeno-(2–4C)alkoxy: 2-fluoroethoxy, 2-chloroethoxy, 2-bromoethoxy, 3-fluoropropoxy and 3-chloropropoxy;
for hydroxy-(2–4C)alkoxy: 2-hydroxyethoxy, 3-hydroxypropoxy and 4-hydroxybutoxy;
for (1–4C)alkoxy-(2–4C)alkoxy: 2-methoxyethoxy, 2-ethoxyethoxy, 3-methoxypropoxy and 3-ethoxypropoxy;
for phenyl-(1–4C)alkoxy: benzyloxy, 2-phenylethoxy and 3-phenylpropoxy;
for halogeno-(2–4C)alkylamino: 2-fluoroethylamino, 2-chloroethylamino, 2-bromoethylamino, 3-fluoropropylamino and 3-chloropropylamino;
for hydroxy-(2–4C)alkylamino: 2-hydroxyethylamino, 3-hydroxypropylamino and 4-hydroxybutylamino;
for (1–4C)alkoxy-(2–4C)alkylamino: 2-methoxyethylamino, 2-ethoxyethylamino, 3-methoxypropylamino and 3-ethoxypropylamino;
for phenyl-(1–4C)alkylamino: benzylamino, phenethylamino and 3-phenylpropylamino;
for (2–4C)alkanoylamino: acetamido, propionamido and butyramido;
for halogeno-(2–4C)alkanoylamino: 2-chloroacetamido, 2-bromoacetamido, 3-chloropropionamido, 3-bromopropionamido and 4-chlorobutyramido;
for hydroxy-(2–4C)alkanoylamino: 2-hydroxyacetamido, 3-hydroxypropionamido and 4-hydroxybutyramido;
for (1–4C)alkoxy-(2–4C) alkanoylamino: 2-methoxyacetamido, 2-ethoxyacetamido, 2-propoxyacetamido, 3-methoxypropionamido, 3-ethoxypropionamido and 4-methoxybutyramido;
for (3–4C)alkenoylamino: acrylamido, methacrylamido, crotonamido and isocrotonamido;
for (3–4C)alkynoylamino: propiolamido;
for N-(1–4C)alkyl-(2–4C)alkanoylamino: N-methylacetamido, N-ethylacetamido and N-methylpropionamido;
for N-(1–4C)alkylbenzamido: N-methylbenzamido;
for N-(1–4C)alkyl-halogeno-( 2–4C)alkanoylamino: 2-chloro-N-methylacetamido, 2-chloro-N-ethylacetamido and 3-chloro-N-methylpropionamido;
for N-(1–4C)alkyl-hydroxy-( 2–4C)alkanoylamino: 2-hydroxy-N-methylacetamido, N-ethyl-2-hydroxyacetamido and 3-hydroxy-N-methylacetamido;
for N-(1–4C)alkyl-(1–4C)alkoxy-( 2–4C)alkanoylamino: 2-methoxy-N-methylacetamido, N-ethyl-2-methoxyacetamido, 2-ethoxy-N-methylacetamido and 2-ethoxy-N-ethylacetamido;
for N-(1–4C)alkyl-(3–4C)alkenoylamino: N-methylacrylamido, N-ethylacrylamido and N-methylmethacrylamido;
for N-(1–4C)alkyl-(3–4C)alkynoylamino: N-methylpropiolamido and N-ethylpropiolamido.

Suitable values for the substituents which may be present on the phenyl ring when $R^1$ is benzamido or N-(1–4C)alkylbenzamido or on a $R^1$ substituent which contains a phenyl group include, for example:
for halogeno: fluoro, chloro and bromo;
for (1–4C)alkyl: methyl, ethyl and propyl;
for (1–4C)alkoxy: methoxy, ethoxy and propoxy.

A suitable value for $R^2$ or $R^3$ when it is halogeno is, for example, fluoro, chloro, bromo or iodo.

A suitable pharmaceutically-acceptable salt of a quinazoline derivative of the invention is, for example, an acid-addition salt of a quinazoline derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a quinazoline derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, quinazoline derivatives of the formula I, or pharmaceutically-acceptable salts thereof, wherein:

(a) $R^1$ is hydroxy, amino, hydroxyamino, trifluoromethoxy, (1–4C)alkoxy, (1–4C)alkylamino, di-[(1–4C)alkyl]amino, aziridin-1-yl, azetidin-1-yl, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, hydroxy-(2–4C)alkylamino, (1–4C)alkoxy-(2–4C)alkylamino, (2–4C)alkanoylamino, 2-oxopyrrolidin-1-yl, halogeno-(2–4C)alkanoylamino, hydroxy-(2–4C)alkanoylamino or (1–4C)alkoxy-(2–4C)alkanoylamino; and n, $R^2$ and $R^3$ have any of the meanings defined hereinbefore or in this section relating to particular novel compounds of the invention;

(b) $R^1$ is amino, hydroxyamino, (1–4C)alkylamino, di-[(1–4C)alkyl]amino, aziridin-1-yl, azetidin-1-yl, pyrrolidin-1-yl, piperidino, morpholino, piperazin-1-yl, 4-(1–4C)alkylpiperazin-1-yl, hydroxy-(2–4C)alkylamino, (1–4C)alkoxy-(2–4C)alkylamino, (2–4C)alkanoylamino, 2-oxopyrrolidin-1-yl, halogeno-(2–4C)alkanoylamino, hydroxy-(2–4C)alkanoylamino or (1–4C)alkoxy-(2–4C)alkanoylamino; and n, $R^2$ and $R^3$ have any of the meanings defined hereinbefore or in this section relating to particular novel compounds of the invention;

(c) $R^1$ is amino, hydroxyamino, (1–4C)alkylamino, di-[(1–4C)alkyl]amino, (2–4C)alkanoylamino, 2-oxopyrrolidin-1-yl, halogeno-(2–4C)alkanoylamino, (3–4C)alkenoylamino, (3–4C)alkynoylamino, $\underline{N}$-(1–4C)alkyl-(2–4C)alkanoylamino and $\underline{N}$-(1–4C)alkyl-halogeno-(2–4C)alkanoylamino; and n, $R^2$ and $R^3$ have any of the meanings defined hereinbefore or in this section relating to particular novel compounds of the invention;

(d) $R^1$ is hydroxy, trifluoromethoxy, (1–4C)alkoxy, (1–4C)alkylthio, halogeno-(2–4C)alkoxy, hydroxy-(2–4C)alkoxy or (1–4C)alkoxy-(2–4C)alkoxy; and n, $R^2$ and $R^3$ have any of the meanings defined hereinbefore or in this section relating to particular novel compounds of the invention; or (e) n is 1 or 2 and each $R^2$ is independently hydrogen, hydroxy, halogeno, trifluoromethyl, amino, nitro, cyano or (1–4C)alkyl; and $R^1$ and $R^3$ have any of the meanings defined hereinbefore or in this section relating to particular novel compounds of the invention.

A further particular compound of the invention is a quinazoline derivative of the formula I
wherein $R^1$ is hydroxy, amino, hydroxyamino, methylamino, ethylamino, dimethylamino, diethylamino, aziridin-1-yl, azetidin-1-yl, pyrrolidin-1-yl, piperidino, morpholino, piperazin-1-yl, 4-methylpiperazin-1-yl, acetamido, propionamido, 2-oxopyrrolidin-1-yl, 2-chloroacetamido, 3-chloropropionamido, 4-chlorobutyramido, 2-hydroxyacetamido or 2-methoxyacetamido;
$R^3$ is fluoro or chloro; and
$(R^2)_n$ is 4'-fluoro, 3'-chloro, 3'-bromo, 3',4'-dichloro, 3'-chloro-4'-fluoro, 3'-trifluoromethyl, 4'-fluoro-3'-trifluoromethyl, 3'-nitro, 4'-chloro-3'-nitro, 4'-fluoro-3'-nitro or 3'-methyl;
or a pharmaceutically-acceptable salt thereof.

A further particular compound of the invention is a quinazoline derivative of the formula I
wherein $R^1$ is hydroxy, amino, hydroxyamino, methylamino, ethylamino, dimethylamino, diethylamino, aziridin-1-yl, azetidin-1-yl, pyrrolidin-1-yl, piperidino, morpholino, piperazin-1-yl, 4-methylpiperazin-1-yl, acetamido, propionamido, 2-oxopyrrolidin-1-yl, 2-chloroacetamido, 3-chloropropionamido, 4-chlorobutyramido, 2-hydroxyacetamido, 2-methoxyacetamido, acrylamido, methacrylamido, N-methylacetamido, $\underline{N}$-ethylacetamido, $\underline{N}$-methylpropionamido, 2-chloro-$\underline{N}$-methylacetamido or 2-chloro-$\underline{N}$-ethylacetamido;
$R^3$ is fluoro or chloro; and
$(R^2)_n$ is 4'-fluoro, 3'-chloro, 3'-bromo, 3',4'-dichloro, 3'-chloro-4'-fluoro, 3'-trifluoromethyl, 4'-fluoro-3'-trifluoromethyl, 3'-nitro, 4'-chloro-3'-nitro, 4'-fluoro-3'-nitro or 3'-methyl;
or a pharmaceutically-acceptable salt thereof.

A further particular compound of the invention is a quinazoline derivative of the formula I
wherein $R^1$ is methoxy, ethoxy, methylthio, 2-chloroethoxy, 2-bromoethoxy, 2-hydroxyethoxy or 2-methoxyethoxy;
$R^3$ is fluoro or chloro; and
$(R^2)_n$ is 4'-fluoro, 3'-chloro, 3'-bromo, 3',4'-dichloro, 3'-chloro-4'-fluoro, 3'-trifluoromethyl, 4'-fluoro-3'-trifluoromethyl, 3'-nitro, 4'-chloro-3'-nitro, 4'-fluoro-3'-nitro or 3'-methyl;
or a pharmaceutically-acceptable salt thereof.

A preferred compound of the invention is a quinazoline derivative of the formula I
wherein $R^1$ is amino, hydroxyamino, methylamino, dimethylamino, acetamido, 2-oxopyrrolidin-1-yl, 2-chloroacetamido or 4-chlorobutyramido;
$R^3$ is fluoro or chloro; and
$(R^2)_n$ is 3'-chloro, 3',4'-dichloro, 3'-chloro-4'-fluoro or 3'-methyl;
or a pharmaceutically-acceptable acid-addition salt thereof.

A further preferred compound of the invention is a quinazoline derivative of the formula I
wherein $R^1$ is amino, hydroxyamino, methylamino, dimethylamino, acetamido, 2-oxopyrrolidin-1-yl, 2-chloroacetamido, 4-chlorobutyramido, acrylamido or 2-chloro-N-methylacetamido;
$R^3$ is fluoro or chloro; and
$(R^2)_n$ is 3'-chloro, 3',4'-dichloro, 3'-chloro-4'-fluoro or 3'-methyl;
or a pharmaceutically-acceptable acid-addition salt thereof.

A further preferred compound of the invention is a quinazoline derivative of the formula I
wherein $R^1$ is methoxy or ethoxy;
$R^3$ is fluoro or chloro; and
$(R^2)_n$ is 3'-chloro, 3',4'-dichloro, 3'-chloro-4'-fluoro or 3'-methyl;
or a pharmaceutically-acceptable acid-addition salt thereof.

A specific preferred compound of the invention is the following quinazoline derivative of the formula I, 6-amino-7-fluoro-4-(3'-methylanilino)quinazoline, 6-(2-chloroacetamido)-7-fluoro-4-(3'-methylanilino)quinazoline, 6-amino-4-(3'-chloro-4'-fluoroanilino)-7-fluoroquinazoline, 7-chloro-6-methylamino-4-(3'-methylanilino)quinazoline, 7-chloro-6-(2-chloroacetamido)-4-(3'-methylanilino)quinazoline or 7-chloro-6-(2-chloroacetamido)-4-(3',4'-dichloroanilino)quinazoline;
or a pharmaceutically-acceptable acid-addition salt thereof.

A further specific preferred compound of the invention is the following quinazoline derivative of the formula I, 7-fluoro-6-hydroxyamino-4-(3'-methylanilino)quinazoline, 4-(3'-chloro-4'-fluoroanilino)-7-fluoro-6-hydroxyamino-quinazoline, 6-acrylamido-7-fluoro-4-(3'-methylanilino)quinazoline, 4-(3'-chloro-4'-fluoroanilino)-7-fluoro-6-methylaminoquinazoline, 6-(2-chloroacetamido)-4-(3'-chloro-4'-fluoroanilino)-7-fluoroquinazoline, 6-(4-chlorobutyramido)-4-(3'-chloro-4'-fluoroanilino)-7-fluoroquinazoline or 4-(3'-chloro-4'-fluoroanilino)-7-fluoro-6-(2-oxopyrrolidin-1-yl)quinazoline;

or a pharmaceutically-acceptable acid-addition salt thereof.

A quinazoline derivative of the formula I, or a pharmaceutically-acceptable salt thereof, may be prepared by any process known to be applicable to the preparation of chemically-related compounds. A suitable process is, for example, illustrated by that used in European Patent Application No. 0 520 722. Such processes, when used to prepare a quinazoline derivative of the formula I, or a pharmaceutically-acceptable salt thereof, are provided as a further feature of the invention and are illustrated by the following representative examples in which, unless otherwise stated, $R^1$, n, $R^2$ and $R^3$ have any of the meanings defined hereinbefore for a quinazoline derivative of the formula I. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a quinazoline of the formula II (set out hereinafter), wherein Z is a displaceable group, with an aniline of the formula III.

A suitable displaceable group Z is, for example, a halogeno, alkoxy, aryloxy or sulphonyloxy group, for example a chloro, bromo, methoxy, phenoxy, methanesulphonyloxy or toluene-p-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide. Alternatively a suitable base is, for example, an alkali metal or alkaline earth metal amide, for example sodium amide or sodium bis(trimethylsilyl)amide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10° to 150° C., preferably in the range 20° to 80° C.

The quinazoline derivative of the formula I may be obtained from this process in the form of the free base or alternatively it may be obtained in the form of a salt with the acid of the formula H-Z wherein Z has the meaning defined hereinbefore. When it is desired to obtain the free base from the salt, the salt may be treated with a suitable base as defined hereinbefore using a conventional procedure.

(b) For the production of those compounds of the formula I wherein $R^1$ or $R^2$ is hydroxy, the cleavage of a quinazoline derivative of the formula I wherein $R^1$ or $R^2$ is (1–4C)alkoxy.

The cleavage reaction may conveniently be carried out by any of the many procedures known for such a transformation. The reaction may be carried out, for example, by treatment of the quinazoline derivative with an alkali metal (1–4C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide. Such reactions are preferably carried out in the presence of a suitable inert solvent or diluent as defined hereinbefore and at a suitable temperature as illustrated in the accompanying Examples.

(c) For the production of those compounds of the formula I wherein $R^1$ is amino or hydroxyamino, the reduction of a quinazoline derivative of the formula I wherein $R^1$ is nitro.

The reduction may conveniently be carried out by any of the many procedures known for such a transformation. The reduction may be carried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

(d) For the production of those compounds of the formula I wherein $R^1$ is (2–4C)alkanoylamino, substituted (2–4C)alkanoylamino, benzamido, (3–4C)alkenoylamino, (3–4C)alkynoylamino, N-(1–4C)alkyl-(2–4C)alkanoylamino, substituted N-(1–4C)alkyl-(2–4C)alkanoylamino, N-(1–4C)alkyl-(3–4C) alkenoylamino, N-(1–4C)alkyl-(2–4C)alkynoylamino or N-(1–4C)alkylbenzamido, or $R^2$ is (2–4C)alkanoylamino, the acylation of a quinazoline derivative of the formula I wherein $R^1$ or $R^2$ is amino.

A suitable acylating agent is, for example, any agent known in the art for the acylation of amino to acylamino, for example an acyl halide, for example a (2–4C)alkanoyl chloride or bromide or a benzoyl chloride or bromide, conveniently in the presence of a suitable base, as defined hereinbefore, an alkanoic acid anhydride or mixed anhydride, for example a (2–4C)alkanoic acid anhydride such as acetic anhydride or the mixed anhydride formed by the reaction of an alkanoic acid and a (1–4C)alkoxycarbonyl halide, for example a (1–4C)alkoxycarbonyl chloride, in the presence of a suitable base as defined hereinbefore. In general the acylation is carried out in a suitable inert solvent or diluent as defined hereinbefore and at a temperature, in the range, for example, –30° to 120° C., conveniently at or near ambient temperature.

(e) For the production of those compounds of the formula I wherein $R^1$ is (1–4C)alkoxy or substituted (1–4C)alkoxy or $R^1$ is (1–4C)alkylamino, di-[(1–4C)alkyl]amino or substituted (1–4C)alkylamino, the alkylation, preferably in the presence of a suitable base as defined hereinbefore, of a quinazoline derivative of the formula I wherein $R^1$ is hydroxy or amino as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–4C)alkyl chloride, bromide or iodide or a substituted (1–4C)alkyl chloride, bromide or iodide, in the presence of a suitable base as defined hereinbefore, in a suitable inert solvent or diluent as defined hereinbefore and at a temperature in the range, for example, 10° to 140° C., conveniently at or near ambient temperature.

When a pharmaceutically-acceptable salt of a quinazoline derivative of the formula I is required, for example an acid-addition salt of a quinazoline derivative of the formula I, it may be obtained, for example, by reaction of said compound with, for example, a suitable acid using a conventional procedure.

As stated hereinbefore the quinazoline derivative defined in the present invention possesses anti-cancer activity which is believed to arise from the receptor tyrosine kinase inhibitory activity of the compound. These properties may be assessed, for example, using one or more of the procedures set out below:

(a) An in vitro assay which determines the ability of a test compound to inhibit the enzyme receptor tyrosine kinase. Receptor tyrosine kinase was obtained in partially purified form from A-431 cells (derived from human vulval carcinoma) by procedures related to those described by Carpenter et. al., *J. Biol. Chem.*, 1979, 254, 4884, Cohen et al., *J. Biol. Chem.*, 1982, 257, 1523 and by Braun et al., *J. Biol. Chem.*, 1984, 259, 2051.

A-431 cells were grown to confluence using Dulbecco's modified Eagle's medium (DMEM) containing 5% fetal calf serum (FCS). The obtained cells were homogenised in a hypotonic borate/EDTA buffer at pH 10.1. The homogenate was centrifuged at 400 g for 10 minutes at 0°–4° C. The supernatant was centrifuged at 25,000 g for 30 minutes at 0°–4° C. The pelleted material was suspended in 30 mM Hepes buffer at pH 7.4 containing 5% glycerol, 4 mM benzamidine and 1% Triton X-100, stirred for 1 hour at 0°–4° C., and recentrifuged at 100,000 g for 1 hour at 0°–4° C. The supernatant, containing solubilised receptor tyrosine kinase, was stored in liquid nitrogen.

For test purposes 40 µl of the enzyme solution so obtained was added to a mixture of 400 µl of a mixture of 150 mM Hepes buffer at pH 7.4, 500 µM sodium orthovanadate, 0.1% Triton X-100, 10% glycerol, 200 µl water, 80 µl of 25 mM DTT and 80µl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 µM solution. Equal volumes of this solution and a solution of epidermal growth factor (EGF; 20 µg/ml) were mixed.

[γ-$^{32}$P]ATP (3000 Ci/mM, 250 µCi) was diluted to a volume of 2 ml by the addition of a solution of ATP (100 µM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 µl) was added to the test enzyme solution (10 µl) and the mixture was incubated at 0°–4° C. for 30 minutes. The ATP/peptide mixture (10 µl) was added and the mixture was incubated at 25° C. for 10 minutes. The phosphorylation reaction was terminated by the addition of 5% trichloroacetic acid (40 µl) and bovine serum albumin (BSA; 1 mg/ml, 5 µl). The mixture was allowed to stand at 4° C. for 30 minutes and then centrifuged. An aliquot (40 µl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an IC$_{50}$ value.

(b) An in vitro assay which determines the ability of a test compound to inhibit the growth of the human nasopharyngeal cancer cell line KB.

KB cells were seeded into wells at a density of 1×10$^4$–1.5×10$^4$ cells per well and grown for 24 hours in DMEM supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An IC$_{50}$ value could then be calculated.

(c) An in vivo assay in a group of male rats which determines the ability of a test compound (usually administered orally as a ball-milled suspension in 0.5% polysorbate) to inhibit the stimulation of liver hepatocyte growth caused by the administration of the growth factor TGFα (400 µg/kg subcutaneously, usually dosed twice, 3 and 7 hours respectively after the administration of the test compound).

In a control group of rats, the administration of TGFα causes on average a 5-fold stimulation of liver hepatocyte growth.

Cell-growth in the control and test animals is determined as follows:

On the morning of the day after the dosing of the test compound (or 0.5% polysorbate in the control group), the animals are dosed with bromodeoxyuridine (BrdU; 100 mg/kg intraperitoneally). The animals are killed four hours later and the livers are excised. Slices are cut from each liver and the uptake of BrdU is determined by a conventional immunohistochemical technique similar to that described on pages 267 and 268 of an article by Goldsworthy et al. in Chemically Induced Cell Proliferation: Implications for Risk Assessment, Wiley-Liss Inc., 1991, pages 253–284.

Further tests were carried out using a range of doses of the test compounds to allow the calculation of an approximate ED$_{50}$ value for the inhibition of liver hepatocyte proliferation as determined by inhibition of the uptake of BrdU.

Although the pharmacological properties of the compounds of the formula I vary with structural change as expected, in general activity possessed by compounds of the formula I may be demonstrated at the following concentrations or doses in one or more of the above tests (a), (b) and (c):

Test (a): $IC_{50}$ in the range, for example, 0.0001–1 μM;

Test (b): $IC_{50}$ in the range, for example, 0.01–10 μM;

Test (c): $ED_{50}$ in the range, for example, 1–100 mg/kg.

Thus, by way of example, the compound 6-amino-7-fluoro- 4-(3'-methylanilino)quinazoline has an $IC_{50}$ of 0.075 μM in Test (a), an $IC_{50}$ of 0.68 μM in Test (b) and an $ED_{50}$ of <40 mg/kg in Test (c); the compound 6-(2-chloroacetamido)-7-fluoro-4-(3'-methylanilino)quinazoline has an $IC_{50}$ of 0.01 μM in Test (a) and an $IC_{50}$ of 0.02 μM in Test (b); and the compound 4-(3'-chloro-4'-fluoroanilino)-7-fluoro-6-methoxyquinazoline has an $IC_{50}$ of 0.07 μM in Test (a), an $IC_{50}$ of 0.53 μM in Test (b) and an $ED_{50}$ of <12.5 mg/kg in Test (c).

According to a further aspect of the invention there is provided a pharmaceutical composition which comprises a quinazoline derivative of the formula I, or a pharmaceutically-acceptable salt thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The quinazoline will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a quinazoline derivative of the formula I as defined hereinbefore for use in a method of treatment of the human or animal body by therapy.

We have now found that the compounds of the present invention possess anti-cancer properties which are believed to arise from their receptor tyrosine kinase inhibitory activity. Accordingly the compounds of the present invention are expected to be useful in the treatment of diseases or medical conditions mediated alone or in part by the enzyme receptor tyrosine kinase, i.e. the compounds may be used to produce a receptor tyrosine kinase inhibitory effect in a warm-blooded animal in need of such treatment. Thus the compounds of the present invention provide a method for treating the proliferation of malignant cells characterised by inhibition of the enzyme receptor tyrosine kinase, i.e. the compounds may be used to produce an anti-proliferative effect mediated alone or in part by the inhibition of the enzyme receptor tyrosine kinase. Accordingly the compounds of the present invention are expected to be useful in the treatment of cancer by providing an anti-proliferative effect, particularly in the treatment of receptor tyrosine kinase sensitive cancers such as cancers of the breast, lung, colon, rectum, stomach, prostate, bladder, pancreas and ovary.

Thus according to this aspect of the invention there is provided the use of a quinazoline derivative of the formula I, or a pharmaceutically-acceptable salt thereof, as defined hereinbefore in the manufacture of a medicament for use in the production of an anti-cancer effect in a warm-blooded animal such as man.

According to a further feature of this aspect of the invention there is provided a method for producing an anti-cancer effect in a warm-blooded animal, such as man, in need of such treatment which comprises administering to said animal an effective amount of a quinazoline derivative as defined immediately above.

As stated above the size of the dose required for the therapeutic or prophylactic treatment of a particular cancer will necessarily be varied depending on the host treated, the route of administration and the severity of the illness being treated. A unit dose in the range, for example, 1–100 mg/kg, preferably 1–50 mg/kg is envisaged.

The anti-cancer treatment defined hereinbefore may be applied as a sole therapy or may involve, in addition to the quinazoline derivative of the invention, one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred antimetabolites disclosed in European Patent Application No. 239362 such as N-{5-[N-(3,4-dihydro-2-methyl- 4-oxoquinazolin-6-ylmethyl)-N-methylamino]-2-thenoyl}-L-glutamic acid; intercalating antibiotics, for example adriamycin and bleomycin; enzymes, for example asparaginase; topoisomerase inhibitors, for example etoposide; biological response modifiers, for example interferon; and anti-hormones, for example antioestrogens such as 'NOLVADEX' (tamoxifen) or, for example antiandrogens such as 'CASODEX' (4'-cyano-3-(4-fluorophenylsulphonyl)-2-hydroxy-2-methyl-3' -(trifluoromethyl)propionanilide. Such conjoint treatment may be achieved by way of the simultaneous, sequential or separate dosing of the individual components of the treatment. According to this aspect of the invention there is provided a pharmaceutical product comprising a quinazoline derivative of the formula I as defined hereinbefore and an additional anti-tumour substance as defined hereinbefore for the conjoint treatment of cancer.

As stated above the quinazoline derivative defined in the present invention is an effective anti-cancer agent, which property is believed to arise from its receptor tyrosine kinase inhibitory properties. Such a quinazoline derivative of the invention is expected to possess a wide range of anti-cancer properties as receptor tyrosine kinases have been implicated in many common human cancers such as leukaemia and breast, lung, colon, rectal, stomach, prostate, bladder, pancreas and ovarian cancer. Thus it is expected that a quinazoline derivative of the invention will possess anti-cancer activity against these cancers. It is in addition expected that a quinazoline of the present invention will possess activity against a range of leukaemias, lymphoid malignancies and solid tumours such as carcinomas and sarcomas in tissues such as the liver, kidney, prostate and pancreas.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet;

(vii) intermediates were not generally fully characterised and purity was assessed by thin layer chromatography (TLC), infra-red (IR) or NMR analysis;

(viii) the following abbreviations have been used:

DMF N,N-dimethylformamide;

DMA N,N-dimethylacetamide.

EXAMPLE 1

A mixture of 7-fluoro-4-(3'-methylanilino)-6-nitroquinazoline (0.25 g), 10% palladium-on-charcoal catalyst (0.03 g) and ethanol (10 ml) was stirred under an atmosphere pressure of hydrogen for 16 hours. The mixture was filtered and the filtrate was evaporated. The residue was triturated under diethyl ether. There was thus obtained 6-amino-7-fluoro-4-(3'-methylanilino)quinazoline (0.18 g), m.p. 205°–206° C.; NMR Spectrum: ($CD_3SOCD_3$) 2.33 (s, 3H), 5.67 (broad s, 2H), 6.9 (m, 1H), 7.24 (m, 1H), 7.4 (d, 1H), 7.6 (m, 3H), 8.3 (s, 1H), 9.35 (broad s, 1H);
Elemental Analysis: Found C, 67.1; H, 4.9; N, 20.8; $C_{15}H_{13}FN_4$ requires C, 67.2; H, 4.9; N, 20.9%.

The 7-fluoro-4-(3'-methylanilino)-6-nitroquinazoline used as a starting material was obtained as follows:

A mixture of 4-fluoroanthranilic acid (15 g) and formamide (30 ml) was stirred and heated to reflux for 6 hours. The mixture was cooled to ambient temperature. The mixture was triturated under water. The solid was isolated, washed with water and dried. There was thus obtained 7-fluoroquinazolin-4-one (13.8 g).

A portion (4 g) of the material so obtained was added portionwise to a stirred mixture of concentrated sulphuric acid (8 ml) and fuming nitric acid (8 ml) which had been cooled to 0° C. The mixture was stirred at ambient temperature for 30 minutes and then heated to 110° C. for 30 minutes. The mixture was cooled to ambient temperature and poured onto a mixture of ice and water. The precipitate was isolated, washed with water and dried. There was thus obtained 7-fluoro-6-nitroquinazolin-4-one (4.3 g), m.p. 268°–270° C.

A mixture of a portion (2.09 g) of the material so obtained, thionyl chloride (16 ml) and DMF (8 drops) was stirred and heated to reflux for 2 hours. The mixture was evaporated, toluene (20 ml) was added and the mixture was re-evaporated. There was thus obtained 4-chloro-7-fluoro-6-nitroquinazoline as a solid which was used without further purification.

A mixture of the solid so obtained, 3'-methylaniline (1.1 ml) and isopropanol (40 ml) was stirred and heated to reflux for 2 hours. The mixture was cooled to ambient temperature and stored at 3° C. for 16 hours. The precipitate was isolated, washed with isopropanol and with diethyl ether and dried. The solid so obtained (2.7 g) was dissolved in a mixture of methylene chloride and methanol and washed with a saturated aqueous sodium bicarbonate solution. The organic phase was washed with water, dried ($MgSO_4$) and evaporated. The residue was purified by column chromatography using a 4:1 mixture of methylene chloride and ethyl acetate as eluent. There was thus obtained 7-fluoro-4-(3'-methylanilino)-6-nitroquinazoline (1.69 g).

EXAMPLE 2

A mixture of 7-fluoro-4-(3'-methylanilino)-6-nitroquinazoline (0.12 g), 10% palladium-on-charcoal catalyst (0.02 g) and ethanol (10 ml) was stirred under an atmosphere pressure of hydrogen for 1 hour. The mixture was filtered and the filtrate was evaporated. The residue was purified by column chromatography using increasingly polar mixtures of methylene chloride and methanol as eluent. The material so obtained was triturated under methanol and the resultant solid was recrystallised from a mixture of methanol and water. There was thus obtained 7-fluoro-6-hydroxyamino-4-(3'-methylanilino)quinazoline (0.051 g), m.p. 228°–230° C.;
NMR Spectrum: ($CD_3SOCD_3$) 2.33 (s, 3H), 6.9 (d, 1H), 7.25 (m, 1H), 7.4 (d, 1H), 7.63 (m, 2H), 8.1 (d, 1H), 8.4 (s, 1H), 8.8 (broad s, 1H), 8.9 (broad s, 1H), 9.7 (broad s, 1H).
Elemental Analysis: Found C, 63.8; H, 4.6; N, 19.6; $C_{15}H_{13}FN_4$ requires C, 63.8; H, 4.5; N, 19.7%.

EXAMPLE 3

Acetic anhydride (0.11 ml) was added to a stirred solution of 6-amino-7-fluoro-4-(3'-methylanilino)quinazoline (0.268 g) in DMA (2 ml) and the mixture was stirred at ambient temperature for 24 hours. Water (10 ml) was added. The precipitate was isolated, washed with water and dried. There was thus obtained 6-acetamido-7-fluoro-4-(3'-methylanilino)quinazoline (0.204 g), m.p. 269°–270° C.;
NMR Spectrum: ($CD_3SOCD_3$) 2.15 (s, 3H), 2.3 (s, 3H), 6.9 (d, 1H), 7.2 (t, 1H), 7.6 (m, 3M), 8.5 (s, 1H), 8.8 (d, 1H), 9.7 (broad s, 1H), 10.0 (broad s, 1H);
Elemental Analysis: Found C, 65.5; H, 4.9; N, 17.9; $C_{17}H_{15}FN_4O$ requires C, 65.8; H, 4.8; N, 18.1%.

EXAMPLE 4

2-Chloroacetyl chloride (0.12 ml) was added to a stirred solution of 6-amino-7-fluoro-4-(3'-methylanilino)quinazoline (0.268 g) in DMA (2 ml) and the mixture was stirred at ambient temperature for 3 hours. The precipitate was isolated and washed with diethyl ether. There was thus obtained 6-(2-chloroacetamido)-7-fluoro-4-(3'-methylanilino)quinazoline hydrochloride (0.315 g), m.p. >320° C.;
NMR Spectrum: ($CD_3SOCD_3$) 2.36 (s, 3H), 4.5 (s, 2H), 7.15 (d, 1H), 7.4 (m, 3H), 7.9 (d, 1H), 8.9 (s, 1H), 9.2 (d, 1H), 10.8 (broad s, 1H), 11.5 (broad s, 1H);
Elemental Analysis: Found C, 54.0; H, 4.2; N, 14.6; $C_{17}H_{14}ClFN_4O$ 1HCl requires C, 53.5; H, 3.9; N, 14.7%.

EXAMPLE 5

4-Chlorobutyryl chloride (0.4 ml) was added to a stirred solution of 6-amino-7-fluoro-4-(3'-methylanilino)quinazoline (0.8 g) in DMA (6 ml) and the mixture was stirred at ambient temperature for 4 hours. The precipitate was isolated and washed with diethyl ether. There was thus obtained 6-(4-chlorobutyramido)-7-fluoro-4-(3'-methylanilino)quinazoline (0.76 g);
NMR Spectrum: (CD$_3$SOCD$_3$) 2.1 (m, 2H), 2.36 (s, 3H), 2.66 (t, 2H), 3.74 (t, 2H), 7.14 (d, 1H), 7.4 (m, 3H), 7.89 (d, 1H), 8.8 (s, 1H), 9.2 (d, 1H), 10.3 (broad s, 1H), 11.4 (broad s, 1H);
Elemental Analysis: Found C, 56.1; H, 4.6; N, 13.7; C$_{19}$H$_{18}$ClFN$_4$O requires C, 55.8; H, 4.7; N, 13.7%.

EXAMPLE 6

A solution of 6-(4-chlorobutyramido)-7-fluoro-4-(3'-methylanilino)quinazoline (0.64 g) in DMA (20 ml) was added to a stirred suspension of sodium hydride (80% dispersion in mineral oil, 0.15 g) in DMA (2 ml). The mixture was stirred at ambient temperature for 20 minutes. The mixture was poured onto ice and extracted with methylene chloride. The organic phase was washed with rarer, dried (MgSO$_4$) and evaporated. The residue was recrystallised from a mixture of methylene chloride and ethyl acetate. There was thus obtained 7-fluoro-4-(3'-methylanilino)-6-(2-oxopyrrolidin-1-yl)quinazoline (0.35 g), m.p. 218°–220° C.;
NMR Spectrum: (CD$_3$SOCD$_3$) 2.2 (m, 2H), 2.35 (s, 3H), 2.5 (m, 2H), 3.9 (t, 2H), 7.0 (m, 1H), 7.3 (m, 1H), 7.6 (m, 3H), 8.56 (s, 1H), 8.65 (m, 1H), 9.75 (broad s, 1H);
Elemental Analysis: Found C, 67.4; H, 5.1; N, 16.5; C$_{19}$H$_{17}$FN$_4$O requires C, 67.8; H, 5.1; N, 16.7%.

EXAMPLE 7

A mixture of 4-(3'-chloro-4'-fluoroanilino)-7-fluoro-6-nitroquinazoline (0.11 g), 30% palladium-on-charcoal catalyst (0.01 g) and acetic acid (10 ml) was stirred under an atmosphere pressure of hydrogen for 30 minutes. The mixture was filtered and the filtrate was evaporated. The residue was triturated under methanol. There was thus obtained 6-amino-4-(3'-chloro-4'-fluoroanilino)-7-fluoroquinazoline (0.037 g), m.p. >250° C.;
NMR Spectrum: (CD$_3$SOCD$_3$) 5.8 (broad s, 2H), 7.4 (m, 2H), 7.75 (d, 1H), 7.8 (m, 1H), 8.1 (m, 1H), 8.4 (s, 1H), 9.7 (broad s, 1H).

The 4-(3'-chloro-4'-fluoroanilino)-7-fluoro-6-nitroquinazoline used as a starting material was obtained by the reaction of 4-chloro-7-fluoro-6-nitroquinazoline and 3'-chloro-4'-fluoroaniline using an analogous procedure to that described in the last paragraph of the portion of Example 1 which is concerned with the preparation of starting materials. There was thus obtained the required starting material.
NMR Spectrum: (CD$_3$SOCD$_3$) 7.5 (t, 1H), 7.8 (m, 2H), 8.1 (m, 1H), 8.7 (s, 1H), 9.6 (d, 1H), 10.5 (broad s, 1H).

EXAMPLE 8

A mixture of 4-(3'-chloro-4'-fluoroanilino)-7-fluoro-6-nitroquinazoline (0.11 g), 30% palladium-on-charcoal catalyst (0.01 g) and ethanol (10 ml) was stirred under an atmosphere pressure of hydrogen for 30 minutes. The mixture was filtered and the filtrate was evaporated. The residue was triturated under methanol. There was thus obtained 4-(3'-chloro-4'-fluoroanilino)-7-fluoro-6-hydroxyaminoquinazoline (0.065 g).
NMR Spectrum: (CD$_3$SOCD$_3$) 7.4 (m, 2H), 7.8 (m, 1H), 8.1 (m, 2H), 8.47 (s, 1H), 8.8 (broad s, 1H), 8.97 (broad s, 1H), 9.85 (broad s, 1H);
Elemental Analysis: Found C, 50.5; H, 3.0; N, 16.2; C$_{14}$H$_8$ClF$_2$N$_4$O 0.75H$_2$O requires C, 50.0; H, 3.1; N, 16.7%.

EXAMPLE 9

Powdered iron (5 g) was added portionwise during 5 minutes to a stirred mixture of 7-chloro-4-(3'-methylanilino)-6-nitroquinazoline (5 g), water (10 ml) and glacial acetic acid (100 ml) which had been warmed to 50° C. The mixture was heated to 50° C. for 2 hours. The mixture was cooled to ambient temperature and filtered. The filtrate was evaporated and the residue was purified by column chromatography using a 9:1 mixture of methylene chloride and methanol as eluent. There was thus obtained 6-amino-7-chloro-4-(3'-methylanilino)quinazoline (2.1 g), m.p. >270° C.;
NMR Spectrum: (CD$_3$SOCD$_3$) 2.35 (s, 3H), 6.0 (broad s, 2H), 7.0 (d, 1H), 7.3 (t, 1H), 7.55 (m, 1H), 7.6 (m, 1H), 7.7 (s, 1H), 7.8 (s, 1H), 8.5 (s, 1H), 10.2 (broad s, 1H).

The 7-chloro-4-(3'-methylanilino)-6-nitroquinazoline used as a starting material was obtained as follows:
A mixture of 4-chloroanthranilic acid (17.2 g) and formamide (10 ml) was stirred and heated to 130° C. for 45 minutes and to 175° C. for 75 minutes. The mixture was allowed to cool to approximately 100° C. and 2-(2-ethoxyethoxy)ethanol (50 ml) was added. The solution so formed was poured into a mixture (250 ml) of ice and water. The precipitate was isolated, washed with water and dried. There was thus obtained 7-chloroquinazolin-4-one (15.3 g, 85%).

A portion (6 g) of the material so obtained was added portionwise to a stirred mixture of concentrated sulphuric acid (12 ml) and fuming nitric acid (12 ml) which had been cooled to 0° C. The mixture was stirred at ambient temperature for 30 minutes and then heated to 110° C. for 30 minutes. The mixture was cooled to ambient temperature and poured onto a mixture of ice and water. The precipitate was isolated, washed with water and dried. There was thus obtained 7-chloro-6-nitroquinazolin-4-one (6.89 g).

A mixture of a portion (4 g) of the material so obtained, thionyl chloride (30 ml), phosphoryl chloride (5 ml) and DMF (10 drops) was stirred and heated to reflux for 4 hours. The mixture was evaporated, toluene (20 ml) was added and the mixture was re-evaporated. There was thus obtained 4,7-dichloro-6-nitroquinazoline as a solid which was used without further purification.

A mixture of the solid so obtained, 3'-methylaniline (1.89 g) and isopropanol (25 ml) was stirred and heated to reflux for 2 hours. The mixture was filtered whilst still hot. The solid so isolated was washed with isopropanol and with diethyl ether and dried. There was thus obtained 7-chloro-4-(3'-methylanilino)-6-nitroquinazoline hydrochloride (3.74 g), m.p. 271°–274° C.

EXAMPLE 10

Glacial acetic acid (0.85 ml) was added to a stirred mixture of 6-amino-7-chloro-4-(3'-methylanilino)quinazoline (1 g), formaldehyde (37% solution in water, 2.28 ml) and ethanol (80 ml). The mixture was stirred at ambient temperature for 10 minutes. Sodium cyanoborohydride (0.443 g) was added portionwise and the mixture was stirred at ambient temperature for 16 hours. The mixture was neutralised by the addition of sodium bicarbonate. The mixture was evaporated and the residue was partitioned between methylene chloride and water. The organic phase was dried (MgSO$_4$) and evaporated. The residue was purified by column chromatography using a 48:1 mixture of methylene chloride and methanol as eluent. There were thus obtained:

7-chloro-6-dimethylamino-4-(3'-methylanilino)quinazoline (0.043 g), m.p. 150°–152° C.;
NMR Spectrum: (CD$_3$SOCD$_3$) 2.35 (s, 3H), 2.9 (s, 6H), 7.0 (d, 1H), 7.3 (t, 1H), 7.6 (m, 2H), 7.8 (s, 1H), 8.07 (s, 1H), 8.47 (s, 1H), 9.7 (broad s, 1H);
and 7-chloro-6-methylamino-4-(3'-methylanilino)quinazoline (0.171 g), m.p. 149°–152° C.;
NMR Spectrum: (CD$_3$SOCD$_3$) 2.35 (s, 3H), 2.95 (d, 3H), 6.03 (m, 1H), 6.9 (d, 1H), 7.26 (t, 1H), 7.36 (s, 1H), 7.6 (s, 1H), 7.65 (broad d, 1H), 7.7 (s, 1H), 8.34 (s, 1H), 9.44 (broad s, 1H).

EXAMPLE 11

Using an analogous procedure to that described in Example 4, 6-amino-7-chloro-4-(3'-methylanilino)quinazoline was reacted with 2-chloroacetyl chloride to give 7-chloro-6-(2-chloroacetamido)-4-(3'-methylanilino)quinazoline hydrochloride in 79% yield;
NMR Spectrum: (CD$_3$SOCD$_3$) 2.35 (s, 3H), 4.5 (s, 2H), 7.15 (d, 1H), 7.4 (t, 1H), 7.5 (m, 2H), 8.15 (s, 1H), 8.88 (s, 1H), 9.02 (s, 1H), 10.55 (broad s, 1H), 11.4 (broad s, 1H).

EXAMPLE 12

Using an analogous procedure to that described in Example 9, 7-chloro-4-(3',4'-dichloroanilino)-6-nitroquinazoline was reduced with iron in acetic acid to give 6-amino-7-chloro-4-(3',4'-dichloroanilino)quinazoline in 20% yield;
NMR Spectrum: (CD$_3$SOCD$_3$) 6.0 (broad s, 2H), 7.65 (m, 2H), 7.8 (m, 2H), 8.22 (d, 1H), 8.55 (s, 1H), 10.25 (broad s, 1H).

The 7-chloro-4-(3',4'-dichloroanilino)-6-nitroquinazoline used as a starting material was obtained by the reaction of 4,7-dichloro-6-nitroquinazoline and 3',4'-dichloroaniline using an analogous procedure to that described in the last paragraph of the portion of Example 9 which is concerned with the preparation of starting materials.

EXAMPLE 13

Using an analogous procedure to that described in Example 4, 6-amino-7-chloro-4-(3',4'-dichloroanilino)quinazoline was reacted with 2-chloroacetyl chloride to give 7-chloro-6-(2-chloroacetamido)-4-( 3',4'-dichloroanilino)quinazoline hydrochloride in 76% yield, m.p.> 280° C.;
NMR Spectrum: (CD$_3$SOCD$_3$) 4.5 (s, 2H), 7.75 (m, 2H), 8.1 (m, 2H), 8.9 (s, 1H), 8.95 (s, 1H), 10.5 (broad s, 1H), 11.3 (broad s, 1H).

EXAMPLE 14

A mixture of 4-chloro-7-fluoro-6-methoxyquinazoline (0.32 g), 3'-methylaniline (0.16 g) and isopropanol (5 ml) was stirred and heated to reflux for 90 minutes. The precipitate was isolated, washed with isopropanol and with diethyl ether and dried. There was thus obtained 7-fluoro-6-methoxy-4-(3'-methylanilino)quinazoline hydrochloride (0.468 g), m.p. 265°–267° C.;
NMR Spectrum: (CD$_3$SOCD$_3$) 2.37 (s, 3H), 4.1 (s, 3H), 7.16 (d, 1H), 7.37 (t, 1H), 7.50 (m, 2H), 7.82 (s, 1H), 8.77 (s, 1H), 8.84 (s, 1H), 11.66 (broad s, 1H);
Elemental Analysis: Found C, 60.2; H, 4.7; N, 13.0; C$_{16}$H$_{14}$FN$_3$O 1HCl requires C, 60.1; H, 4.7; N, 13.1%.

The 4-chloro-7-fluoro-6-methoxyquinazoline used as a starting material was obtained as follows:
Concentrated nitric acid (70%, 4.8 ml) was added dropwise during 20 minutes to a stirred mixture of methyl 4-fluoro-3-methoxybenzoate (14 g) and concentrated sulphuric acid (140 ml) which had been cooled to −10° C. The mixture was allowed to warm to 5° C. and was stirred at that temperature for 15 minutes. The mixture was poured onto ice and extracted with ethyl acetate. The organic phase was washed with water, dried (MgSO$_4$) and evaporated. The residue was purified by column chromatography using increasingly polar mixtures of hexane and methylene chloride as eluent. There was thus obtained methyl 4-fluoro-5-methoxy-2-nitrobenzoate (11.8 g).

A mixture of a portion (10.3 g) of the material so obtained, 10% palladium-on-charcoal catalyst (1 g) and ethanol (500 ml) was stirred under an atmosphere pressure of hydrogen for 3 hours. The mixture was filtered and the filtrate was evaporated. There was thus obtained 4-fluoro-5-methoxyanthranilic acid methyl ester (9 g).

Using analogous procedures to those described in the first and third paragraphs of the portion of Example 1 which is concerned with the preparation of starting materials, 4-fluoro-5-methoxyanthranilic acid methyl ester was converted into 4-chloro-7-fluoro-6-methoxyquinazoline in 30% yield.

EXAMPLE 15 using an analogous procedure to that described in Example 14, 4-chloro-7-fluoro-6-methoxyquinazoline was reacted with 3'-chloro-4'-fluoroaniline to give 4-(3'-chloro-4'-fluoroanilino)-7-fluoro-6-methoxyquinazoline hydrochloride in 80% yield, m.p. 274°–275° C.;
NMR Spectrum: (CD$_3$SOCD$_3$) 4.08 (s, 3H), 7.54 (m, 1H), 7.77 (m, 2H), 8.04 (m, 1H), 8.60 (d, 1H), 8.86 (s, 1H).
Elemental Analysis: Found C, 50.5; H, 3.1; N, 11.3; C$_{15}$H$_{10}$ClF$_2$N$_3$O 1HCl requires C, 50.3; H, 3.1; N, 11.7%.

EXAMPLE 16

Glacial acetic acid (0.46 ml) was added to a stirred mixture of 6-amino-7-fluoro-4-(3'-methylanilino)quinazoline (1.07 g), formaldehyde (37% solution in water, 0.7 ml) and ethanol (100 ml) and the mixture was stirred at ambient temperature for 5 minutes. Sodium cyanoborohydride (0.51 g) was added portionwise and the mixture was stirred at ambient temperature for 24 hours. The mixture was evaporated and the residue was neutralised by the addition of a saturated aqueous sodium bicarbonate solution. The mixture was partitioned between methylene chloride and water. The organic phase was washed with water, dried (MgSO$_4$) and evaporated. The residue was purified by column chromatography using a 9:1 mixture of methylene chloride and methanol as eluent. There was thus obtained 7-fluoro-6-methylamino-4-(3'-methylanilino)quinazoline as a solid (0.62 g);
NMR Spectrum: (CD$_3$SOCD$_3$) 2.3 (s, 3H), 2.9 (d, 3H), 6.2 (d, 1H), 6.95 (d, 1H), 7.25 (t, 1H), 7.4 (m, 2H), 7.6 (m, 2H), 8.3 (s, 1H), 9.4 (broad s, 1H).

EXAMPLE 17

Using an analogous procedure to that described in Example 16, 6-amino-7-fluoro-4-(3'-methylanilino)quinazoline (0.268 g) was reacted with formaldehyde (37% solution in water, 0.65 ml) and sodium cyanoborohydride (0.126 g) for 24 hours. Second portions of the same quantities of formaldehyde and sodium cyanoborohydride were added and the reaction was continued for 24 hours. Third portions of the same quantities of the two reagents were added and the reaction was continued for a further 24 hours.

The reaction mixture was worked up using an analogous procedure to that described in Example 16. There was thus obtained 7-fluoro-6-dimethylamino-4-(3'-methylanilino)quinazoline as a solid (0.132 g);
NMR Spectrum: (CD$_3$SOCD$_3$) 2.3 (s, 3H), 2.9 (s, 6H), 6.99 (d, 1H), 7.3 (t, 1H), 7.45 (d, 1H), 7.6 (m, 2H), 7.8 (d, 1H), 8.45 (s, 1H), 9.65 (broad s, 1H).

EXAMPLE 18

Using an analogous procedure to that described in Example 4, 7-fluoro-6-methylamino-4-(3'-methylanilino)quinazoline was reacted with 2-chloroacetyl chloride to give 6-(2-chloro-N-methylacetamido)-7-fluoro-4-(3'-methylanilino)quinazoline hydrochloride (0.097 g);
NMR Spectrum: (CD$_3$SOCD$_3$+ CD$_3$CO$_2$D, at 100° C.) 2.3 (s, 3H), 3.4 (s, 3H), 4.2 (s, 2H), 7.1 (d, 1H), 7.3 (t, 1H), 7.5 (m, 2H), 7.7 (d, 1H), 8.7 (s, 1H), 8.9 (d, 1H).

EXAMPLE 19

Acryloyl chloride (0.1 ml) was added to a stirred solution of 6-amino-7-fluoro-4-(3'-methylanilino)quinazoline (0.268 g) in DMA (2 ml) and the mixture was stirred at ambient temperature for 2 hours. Diethyl ether was added to the mixture and the resultant precipitate was isolated and washed with diethyl ether. The solid was dissolved in a mixture of methylene chloride and methanol and the solution was washed with a saturated aqueous sodium bicarbonate solution. The organic phase was dried (MgSO$_4$) and evaporated. The residue was purified by column chromatography using a 9:1 mixture of methylene chloride and methanol as eluent. There was thus obtained 6-acrylamido-7-fluoro-4-(3'-methylanilino)quinazoline as a solid (0.062 g);
NMR Spectrum: (CD$_3$SOCD$_3$) 2.3 (s, 3H), 5.9 (m, 1H), 6.4 (m, 1H), 6.7 (m, 1H), 7.0 (d, 1H), 7.3 (m, 1H), 7.6 (m, 3H), 8.5 (s, 1H), 9.0 (d, 1H), 9.8 (broad s, 1H), 10.2 (broad s, 1H).

EXAMPLE 20

Using an analogous procedure to that described in Example 16, 6-amino-4-(3'-chloro-4'-fluoroanilino)-7-fluoroqutnazoline was reacted with sodium cyanoborohydride to give 4-(3'-chloro-4'-fluoroanilino)-7-fluoro-6-methylaminoquinazoline as a solid in 19% yield;
NMR Spectrum: (CD$_3$SOCD$_3$) 2.9 (d, 3H), 6.3 (broad s, 1H), 7.4 (m, 3H), 7.8 (m, 1H), 8.1 (m, 1H), 8.4 (s, 1H), 9.5 (broad s, 1H).

EXAMPLE 21

Using an analogous procedure to that utilised in Example 17, 6-amino-4-(3'-chloro-4'-fluoroanilino)-7-fluoroquinazoline was reacted with sodium cyanoborohydride to give 4-(3'-chloro-4'-fluoroanilino)-6-dimethylamino-7-fluoroquinazoline as a solid in 29% yield;
NMR Spectrum: 2.95 (s, 6H), 7.5 (m, 2H), 7.75 (m, 2H), 8.1 (m, 1H), 8.5 (s, 1H), 9.7 (broad s, 1H).

EXAMPLE 22

Using an analogous procedure to that described in Example 4, 6-amino-4-(3'-chloro-4'-fluoroanilino)-7-fluoroquinazoline was reacted with 2-chloroacetyl chloride to give a precipitate which was isolated. The solid was dissolved in methylene chloride and triethylamine was added. The precipitate was isolated and purified by column chromatography using a 1:1 mixture of methylene chloride and acetone as eluent. There was thus obtained 6-(2-chloroacetamido)-4-(3'-chloro-4'-fluoroanilino)-7-fluoroquinazoline as a solid in 23% yield;
NMR Spectrum: (CD$_3$SOCD$_3$) 4.4 (s, 2H), 7.45 (t, 1H), 7.7 (d, 1H), 7.8 (m, 1H), 8.1 (m, 1H), 8.6 (s, 1H), 8.9 (d, 1H), 10.1 (broad s, 1H), 10.4 (s, 1H).

EXAMPLE 23

Using an analogous procedure to that described in Example 5, 6-amino-4-(3'-chloro-4'-fluoroanilino)-7-fluoroquinazoline was reacted with 4-chlorobutyryl chloride to give 6-(4-chlorobutyramido)-4-(3'-chloro-4'-fluoroanilino)-7-fluoroquinazoline hydrochloride as a solid in 91% yield;
NMR Spectrum: (CD$_3$SOCD$_3$) 2.15 (m, 2H), 2.7 (t, 2H), 3.8 (t, 2H), 7.55 (t, 1H), 7.7 (m, 1H), 7.9 (d, 1H), 8.0 (m, 1H), 8.9 (s, 1H), 9.15 (d, 1H), 10.4 (broad s, 1H), 11.5 (broad s, 1H).

EXAMPLE 24

A solution of 6-(4-chlorobutyramido)-4-(3'-chloro-4'-fluoroanilino)-7-fluoroquinazoline hydrochloride (0.64 g) in DMA (6 ml) was added to a stirred suspension of sodium hydride [80% dispersion in mineral oil (0.14 g) from which the oil was washed using hexane] in DMA (2 ml). The mixture was stirred at ambient temperature for 1 hour. A mixture of ice and water (40 ml) was added and the resultant mixture was stirred for 30 minutes. The precipitate was isolated, washed with water, a small amount of isopropanol and diethyl ether and dried. The solid was purified by column chromatography using a 9:1 mixture of methylene chloride and methanol as eluent. There was thus obtained 4-(3'-chloro-4'-fluoroanilino)-7-fluoro-6-(2-oxopyrrolidin-1-yl)quinazoline as a solid (0.13 g);
NMR Spectrum: (CD$_3$SOCD$_3$) 2.2 (m, 2H), 2.5 (m, 2H), 3.9 (t, 2H), 7.5 (t, 1H), 7.7 (d, 1H), 7.8 (m, 1H), 8.15 (m, 1H), 8.6 (m, 2H), 9.9 (broad s, 1H).

EXAMPLE 25

A mixture of 4,7-dichloro-6-methoxyquinazoline (1.19 g), 3'-chloro-4'-fluoroaniline (0.76 g) and isopropanol (25 ml) was stirred and heated to reflux for 2 hours. The mixture was cooled to ambient temperature. The precipitate was filtered off. The solid was dissolved in a 9:1 mixture of methylene chloride and methanol and the solution was washed with a saturated aqueous sodium bicarbonate solution. The organic phase was dried (MgSO$_4$) and evaporated. The residue was purified by column chromatography using a 9:1 mixture of methylene chloride and ethyl acetate as eluent. There was thus obtained 7-chloro-4-(3'-chloro-4'-fluoroanilino)-6-methoxyquinazoline (0.32 g), m.p. 223°–224° C.;
Elemental Analysis: Found C, 53.0; H, 2.8; N, 12.2;
C$_{15}$H$_{10}$Cl$_2$FN$_3$O requires C, 53.5; H, 3.0; N, 12.4%.
The 4,7-dichloro-6-methoxyquinazoline used as a starting material was obtained as follows:
A mixture of 7-hydroxy-6-methoxy-4-(3'-methylanilino)quinazoline [European Patent Application No. 0 566 226 (Example 19 thereof); 8.3 g], concentrated hydrochloric acid (100 ml) and ethanol (100 ml) was stirred and heated to reflux for 72 hours. The mixture was evaporated, water (50 ml) was added and the mixture was basified by the addition of a saturated aqueous ammonium hydroxide solution. The precipitate was isolated, washed with water and dried. There was thus obtained 4,7-dihydroxy-6-methoxyquinazoline (4 g).

A mixture of 4,7-dihydroxy-6-methoxyquinazoline (1 g) and thionyl chloride (14 ml) was heated to reflux for 2 hours. The mixture was evaporated to give 4,7-dichloro-6-methoxyquinazoline which was used without further purification.

CHEMICAL FORMULAE

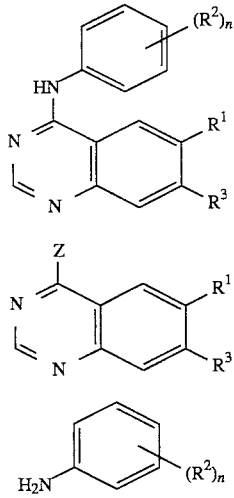

I claim:

1. A quinazoline derivative of the formula I

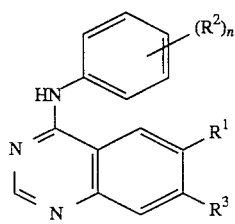

wherein $R^1$ is hydroxy, amino, hydroxyamino, trifluoromethoxy, (1–4C)alkoxy, (1–4C)alkylamino, di-[(1–4C)alkyl]amino, aziridin-1-yl, azetidin-1-yl, pyrrolidin-1-yl, piperidino, morpholino, piperazin-1-yl, 4-(1–4C)alkylpiperazin-1-yl, (1–4C)alkylthio, halogeno-(2–4C)alkoxy, hydroxy-(2–4C)alkoxy, (1–4C)alkoxy-(2–4C)alkoxy, phenyl-(1–4C)alkoxy, halogeno-(2–4C)alkylamino, hydroxy-(2–4C)alkylamino, (1–4C)alkoxy-(2–4C)alkylamino, phenyl-(1–4C)alkylamino, (2–4C)alkanoylamino, benzamido, 2-oxopyrrolidin-1-yl, 2-oxopiperidin-1-yl, halogeno-(2–4C)alkanoylamino, hydroxy-(2–4C)alkanoylamino, (1–4C)alkoxy-(2–4C)alkanoylamino, (3–4C)alkenoylamino, (3–4C)alkynoylamino, N-(1–4C)alkyl-(2–4C)alkanoylamino, N-(1–4C)alkylbenzamido, N-(1–4C)alkyl-halogeno-(2–4C)alkanoylamino, N-(1–4C)alkyl-hydroxy-(2–4C)alkanoylamino, N-(1–4C)alkyl-(1–4C)alkoxy(2–4C)alkanoylamino, N-(1–4C)alkyl-(3–4C)alkenoylamino or N-(1–4C)alkyl-(3–4C)alkynoylamino, and wherein said benzamido or N-(1–4C)alkylbenzamido substituent or any phenyl group in a $R^1$ substituent may optionally bear one or two halogeno, (1–4C)alkyl or (1–4C)alkoxy substituents; $R^3$ is halogeno; and n is the integer 1, 2 or 3 and each $R^2$ is independently hydrogen, hydroxy, halogeno, trifluoromethyl, amino, nitro, cyano, (1–4C)alkyl, (1–4C)alkoxy or (2–4C)alkanoylamino; or a pharmaceutically-acceptable salt thereof.

2. A quinazoline derivative of the formula I as claimed in claim 1 wherein $R^1$ is hydroxy, amino, hydroxyamino, methylamino, ethylamino, dimethylamino, diethylamino, aziridin-1-yl, azetidin-1-yl, pyrrolidin-1-yl, piperidino, morpholino, piperazin-1-yl, 4-methylpiperazin-1-yl, acetamido, propionamido, 2-oxopyrrolidin-1-yl, 2-chloroacetamido, 3-chloropropionamido, 4-chlorobutyramido, 2-hydroxyacetamido or 2-methoxyacetamido;
$R^3$ is fluoro or chloro; and
$(R^2)_n$ is 4'-fluoro, 3'-chloro, 3'-bromo, 3',4'-dichloro, 3'-chloro-4'-fluoro, 3'-trifluoromethyl, 4'-fluoro-3'-trifluoromethyl, 3'-nitro, 4'-chloro-3'-nitro, 4'-fluoro-3'-nitro or 3'-methyl;
or a pharmaceutically-acceptable salt thereof.

3. A quinazoline derivative of the formula I as claimed in claim 1 wherein $R^1$ is hydroxy, amino, hydroxyamino, methylamino, ethylamino, dimethylamino, diethylamino, aziridin-1-yl, azetidin-1-yl, pyrrolidin-1-yl, piperidino, morpholino, piperazin-1-yl, 4-methylpiperazin-1-yl, acetamido, propionamido, 2-oxopyrrolidin-1-yl, 2-chloroacetamido, 3-chloropropionamido, 4-chlorobutyramido, 2-hydroxyacetamido, 2-methoxyacetamido, acrylamido, methacrylamido, N-methylacetamido, N-ethylacetamido, N-methylpropionamido, 2-chloro-N-methylacetamido or 2-chloro-N-ethylacetamido;
$R^3$ is fluoro or chloro; and
$(R^2)_n$ is 4'-fluoro, 3'-chloro, 3'-bromo, 3',4'-dichloro, 3'-chloro-4'-fluoro, 3'-trifluoromethyl, 4'-fluoro-3'-trifluoromethyl, 3'-nitro, 4'-chloro-3'-nitro, 4'-fluoro-3'-nitro or 3'-methyl;
or a pharmaceutically-acceptable salt thereof.

4. A quinazoline derivative of the formula I as claimed in claim 1 wherein $R^1$ is methoxy, ethoxy, methylthio, 2-chloroethoxy, 2-bromoethoxy, 2-hydroxyethoxy or 2-methoxyethoxy;
$R^3$ is fluoro or chloro; and
$(R^2)_n$ is 4'-fluoro, 3'-chloro, 3'-bromo, 3',4'-dichloro, 3'-chloro-4'-fluoro, 3'-trifluoromethyl, 4'-fluoro-3'-trifluoromethyl, 3'-nitro, 4'-chloro-3'-nitro, 4'-fluoro-3'-nitro or 3'-methyl;
or a pharmaceutically-acceptable salt thereof.

5. A quinazoline derivative of the formula I as claimed in claim 1 wherein $R^1$ is amino, hydroxyamino, methylamino, dimethylamino, acetamido, 2-oxopyrrolidin-1-yl, 2-chloroacetamido or 4-chlorobutyramido;
$R^3$ is fluoro or chloro; and
$(R^2)_n$ is 3'-chloro, 3',4'-dichloro, 3'-chloro-4'-fluoro or 3'-methyl;
or a pharmaceutically-acceptable acid-addition salt thereof.

6. A quinazoline derivative of the formula I as claimed in claim 1 wherein R is amino, hydroxyamino, methylamino, dimethylamino, acetamido, 2-oxopyrrolidin-1-yl, 2-chloroacetamido, 4-chlorobutyramido, acrylamido or 2-chloro-N-methylacetamido;
$R^3$ is fluoro or chloro; and
$(R^2)_n$ is 3'-chloro, 3',4'-dichloro, 3'-chloro-4'-fluoro or 3'-methyl;
or a pharmaceutically-acceptable acid-addition salt thereof.

7. A quinazoline derivative of the formula I as claimed in claim 1 wherein $R^1$ is methoxy or ethoxy;
$R^3$ is fluoro or chloro; and
$(R^2)_n$ is 3'-chloro, 3',4'-dichloro, 3'-chloro-4'-fluoro or 3'-methyl;
or a pharmaceutically-acceptable acid-addition salt thereof.

8. A quinazoline derivative of the formula I as claimed in claim 1 selected from 6-amino-7-fluoro-4-(3'-methylanilino)quinazoline, 6-(2-chloroacetamido)-7-fluoro-4-(3'-methylanilino)quinazoline, 6-amino-4-(3'-chloro-4'-fluoroanilino)-7-fluoroquinazoline, 7-chloro-6-methylamino-4-(3'-methylanilino)quinazoline, 7-chloro-6-(2-chloroacetamido)-4-(3'-methylanilino)quinazoline and 7-chloro-6-(2-chloroacetamido)-4-(3',4'-dichloroanilino)quinazoline;
or a pharmaceutically-acceptable acid-addition salt thereof.

9. A quinazoline derivative of the formula I as claimed in claim 1 selected from 7-fluoro-6-hydroxyamino-4-(3'-methylanilino)quinazoline, 4-(3'-chloro-4'-fluoroanilino)-7-fluoro-6-hydroxyaminoquinazoline, 6-acrylamido-7-fluoro-4-(3'-methylanilino)quinazoline, 4-(3'-chloro-4'-fluoroanilino)-7-fluoro-6-methylaminoquinazoline, 6-(2-chloroacetamido)-4-(3'-chloro-4'-fluoroanilino)-7-fluoroquinazoline, 6-(4-chlorobutyramido)-4-(3'-chloro-4'-fluoroanilino)-7-fluoroquinazoline and 4-(3'-chloro-4'-fluoroanilino)-7-fluoro-6-(2-oxopyrrolidin-1-yl)quinazoline;
or a pharmaceutically-acceptable acid-addition salt thereof.

10. A method for producing in a warm-blooded animal an inhibitory effect against the EGF-type of receptor tyrosine kinase enzymes which comprises administering to said animal an effective amount of a quinazoline derivative of the formula I, or a pharmaceutically acceptable salt thereof, as claimed in any one of claims 1 to 9.

11. A pharmaceutical composition which comprises a quinazoline derivative of the formula I, or a pharmaceutically-acceptable salt thereof, as claimed in any one of claims 1 to 9 in association with a pharmaceutically-acceptable diluent or carrier.

12. A method for producing an anti-cancer effect in a warm-blooded animal in need of such treatment which comprises administering to said animal an effective amount of a quinazoline derivative of the formula I, or a pharmaceutically-acceptable salt thereof, as claimed in any one of claims 1 to 9.

13. A method for producing an anti-cancer effect in a warm-blooded animal having a cancer which is sensitive to inhibition of the EGF-type of receptor tyrosine kinase enzymes which comprises administering to said animal an effective amount of a quinazoline derivative of the formula I, or a pharmaceutically-acceptable salt thereof, as claimed in any one of claims 1 to 9.

14. A method for producing an anti-proliferative effect in a warm-blooded animal having a cancer which is sensitive to inhibition of the EGF-type of receptor tyrosine kinase enzymes which comprises administering to said animal an effective amount of a quinazoline derivative of the formula I, or a pharmaceutically-acceptable salt thereof, as claimed in any one of claims 1 to 9.

15. A method for aiding the regression or palliation in a warm-blooded animal of a cancer which is sensitive to inhibition of the EGF-type of receptor tyrosine kinase enzymes which comprises administering to said animal an effective amount of a quinazoline derivative of the formula I, or a pharmaceutically-acceptable salt thereof, as claimed in any one of claims 1 to 9.

* * * * *